(12) United States Patent
Takamatsu et al.

(10) Patent No.: US 8,450,551 B2
(45) Date of Patent: May 28, 2013

(54) METHOD FOR PRODUCING PROPYLENE

(75) Inventors: Yoshikazu Takamatsu, Tokyo (JP); Ryusuke Miyazaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/254,373

(22) PCT Filed: Mar. 1, 2010

(86) PCT No.: PCT/JP2010/053265
§ 371 (c)(1),
(2), (4) Date: Sep. 1, 2011

(87) PCT Pub. No.: WO2010/101121
PCT Pub. Date: Sep. 10, 2010

(65) Prior Publication Data
US 2012/0004490 A1    Jan. 5, 2012

(30) Foreign Application Priority Data
Mar. 2, 2009    (JP) .................................. 2009-048369

(51) Int. Cl.
C07C 6/00    (2006.01)
(52) U.S. Cl.
USPC .......................................... 585/643; 585/638
(58) Field of Classification Search
USPC ................................................. 585/643, 638
See application file for complete search history.

(56) References Cited

U.S. PATENT DOCUMENTS

| | | | |
|---|---|---|---|
| 4,150,062 A * | 4/1979 | Garwood et al. | 585/415 |
| 4,524,055 A * | 6/1985 | Onodera et al. | 423/700 |
| 4,527,001 A * | 7/1985 | Kaiser | 585/643 |
| 4,605,807 A * | 8/1986 | Mazurek | 585/517 |
| 4,627,968 A * | 12/1986 | Kai | 423/703 |
| 4,845,063 A * | 7/1989 | Chu | 502/60 |

(Continued)

FOREIGN PATENT DOCUMENTS

| | | |
|---|---|---|
| JP | 03-293031 | 12/1991 |
| JP | 05-147925 | 6/1993 |

(Continued)

OTHER PUBLICATIONS

International Preliminary Report on Patentability dated Sep. 22, 2011 issued in corresponding International Application No. PCT/JP2010/053265.

(Continued)

*Primary Examiner* — In Suk Bullock
*Assistant Examiner* — Bradley Etherton
(74) *Attorney, Agent, or Firm* — Finnegan, Henderson, Farabow, Garrett & Dunner, L.L.P.

(57) ABSTRACT

The present invention provides in a method for producing propylene from a hydrocarbon raw material containing ethylene in an amount exceeding 50% by mass under the co-existence of water, a method for producing propylene stably over a long term from ethylene in a high yield and with the reaction/regeneration repeated. A method for producing propylene includes a step for catalytically converting a hydrocarbon raw material containing ethylene in an amount exceeding 50% by mass with a zeolite-containing catalyst while supplying water, wherein a zeolite contained in the zeolite-containing catalyst satisfies (1) to (3) shown below;

(1) the zeolite is an MFI zeolite,
(2) a zeolite crystallization index obtained from an X-ray diffraction spectrum is 3.3 or more, and
(3) a molar ratio of silica/alumina ($SiO_2/Al_2O_3$) is 20 to 300.

6 Claims, 13 Drawing Sheets

Example 1

U.S. PATENT DOCUMENTS

| | | | |
|---|---|---|---|
| 4,849,194 A * | 7/1989 | Krishnamurthy et al. | 423/700 |
| 6,388,161 B1 | 5/2002 | Dath et al. | |
| 2004/0054169 A1 | 3/2004 | Tsunoda et al. | |
| 2006/0229482 A1 | 10/2006 | Setoyama et al. | |
| 2007/0129236 A1 * | 6/2007 | Liu et al. | 502/74 |
| 2010/0204532 A1 | 8/2010 | Minoura et al. | |
| 2010/0222203 A1 | 9/2010 | Baba et al. | |

FOREIGN PATENT DOCUMENTS

| | | |
|---|---|---|
| JP | 07-291620 | 11/1995 |
| JP | 10-52646 | 2/1998 |
| JP | 2001-031979 | 2/2001 |
| JP | 2005-232122 | 9/2005 |
| JP | 2005-281254 | 10/2005 |
| JP | 2006-335730 | 12/2006 |
| JP | 2007-191444 | 8/2007 |
| WO | WO 02/064560 A1 | 8/2002 |
| WO | WO 2007/114195 A1 | 10/2007 |
| WO | WO 2009/031445 A1 | 3/2009 |

OTHER PUBLICATIONS

English-Language Translation of Japanese Search Report for International Application No. PCT/JP2010/053265, mailing dated Jun. 8, 2010.

* cited by examiner

|  | MFI Zeolite | | | | TiO2 | Crystallization index |
|---|---|---|---|---|---|---|
| Peak No. | 1 | 2 | 3 | 4 | IS | 3.73 |
| 2θ (deg) | 23.06 | 23.22 | 23.70 | 23.90 | 27.42 | |
| Intensity (CPS) | 6354 | 6491 | 2652 | 2096 | 4714 | |

|  | MFI Zeolite | | | | TiO2 | Crystallization index |
|---|---|---|---|---|---|---|
| Peak No. | 1 | 2 | 3 | 4 | IS | |
| 2θ (deg) | 23.06 | 23.22 | 23.70 | 23.90 | 27.42 | 4.45 |
| Intensity (CPS) | 6703 | 8778 | 3625 | 2646 | 4885 | |

|  | MFI Zeolite | | | | TiO2 | Crystallization index |
|---|---|---|---|---|---|---|
| Peak No. | 1 | 2 | 3 | 4 | IS | |
| 2θ (deg) | 23.06 | 23.22 | 23.70 | 23.90 | 27.42 | 3.37 |
| Intensity (CPS) | 6601 | 5351 | 2236 | 2333 | 4904 | |

|  | MFI Zeolite | | | | TiO2 | Crystallization index |
| --- | --- | --- | --- | --- | --- | --- |
| Peak No. | 1 | 2 | 3 | 4 | IS | |
| 2θ (deg) | 23.06 | 23.22 | 23.70 | 23.90 | 27.42 | 2.84 |
| Intensity (CPS) | 5463 | 4630 | 1776 | 1920 | 4858 | |

|  | MFI Zeolite | | | | TiO2 | Crystallization index |
|---|---|---|---|---|---|---|
| Peak No. | 1 | 2 | 3 | 4 | IS | |
| 2θ (deg) | 23.06 | 23.22 | 23.70 | 23.90 | 27.42 | 4.37 |
| Intensity (CPS) | 8595 | 6740 | 2370 | 3753 | 4905 | |

|  | MFI Zeolite | | | | TiO2 | Crystallization index |
|---|---|---|---|---|---|---|
| Peak No. | 1 | 2 | 3 | 4 | IS | |
| 2θ (deg) | 23.06 | 23.22 | 23.70 | 23.90 | 27.42 | 2.90 |
| Intensity (CPS) | 5571 | 3176 | 1781 | 3518 | 4840 | |

METHOD FOR PRODUCING PROPYLENE

TECHNICAL FIELD

The present invention relates to a method for producing propylene from a hydrocarbon raw material containing ethylene by using a zeolite-containing catalyst.

BACKGROUND ART

Several methods have been known which produce propylene from an olefins-containing hydrocarbon raw material by using a zeolite-containing catalyst. Examples known as zeolite-containing catalysts for use in the production of propylene from olefins include a catalyst in which Ag is contained in an intermediate pore size zeolite that substantially does not contain protons and a catalyst in which the silica/alumina ($SiO_2/Al_2O_3$) molar ratio thereof falls within a range from 200 to 5000.

Although the term "olefins" covers a broad concept, the "olefins" that have hitherto been used as raw materials for the production of propylene are limited to the olefins having four or more carbon atoms. However, some documents describe that raw materials other than the aforementioned olefins can be used.

For example, Japanese Patent Laid-Open No. 2001-31979 describes "a method including contacting a hydrocarbon feedstock containing one or more olefinic components of $C_4$ or greater with a crystalline silicate catalyst to produce an effluent having a second composition of one or more olefinic components of $C_3$ or greater, the feedstock and the effluent having substantially the same olefin content" (claim 1), and also describes that "preferably, the ethylene comprises from 0.1 to 50 wt % of the hydrocarbon feedstock" (paragraph 0028).

Japanese Patent Laid-Open No. 2006-335730 describes a method for producing propylene from ethylene and methanol and/or dimethyl ether.

Japanese Patent Laid-Open No. 2007-191444 describes a method for producing propylene from ethanol (that is, ethylene and water generated via a dehydration reaction) with, as a solid acid catalyst, an H-ZSM5 zeolite in which metal ions are introduced or a phosphate zeolite such as SAPO-34.

CITATION LIST

Patent Literature
Patent Literature 1: JP-A-2001-31979
Patent Literature 2: JP-A-2006-335730
Patent Literature 3: JP-A-2007-191444

SUMMARY OF INVENTION

Technical Problem

A method for producing propylene from ethylene is advantageous from the cost point of view in some cases and the Japanese Patent Laid-Open Nos. 2001-31979 and 2006-335730 describe that propylene can be produced from a raw material containing ethylene. In spite of the advantages, the foregoing methods have not yet been put into practical use. Reasons why the methods have not yet been put into practical use may be considered ascribable to the facts that so-far proposed catalysts could not achieve sufficient activity for converting stable ethylene with the selectivity maintained high.

On the other hand, Japanese Patent Laid-Open No. 2007-191444 discloses a method for producing propylene from ethanol as a raw material. That is, it is described that a phosphate zeolite exhibits high selectivity when propylene is produced from a mixed raw material of ethylene and water generated by a dehydration reaction of ethanol. However, according to an example where a phosphate zeolite is used as a catalyst, a rate of conversion of ethylene is such low as 40% or less and the rate of conversion becomes remarkably lower within only a few hours. It is not said that such a catalyst of which activity degrades in a short time can be industrially used.

When propylene is industrially produced, a method where ethylene obtained by steam cracking of ethane is used as it is as a raw material without separating and purifying and a method where ethanol derived from biomass is used as a raw material ethylene source are advantageous. That is, from the viewpoint of easy availability of a raw material, it can be said a preferable embodiment to be able to feed an ethylene source to a reaction system with water contained in the ethylene source.

However, according to the investigations of the present inventors, a problem has been found that when water co-exists in a reaction system, since a zeolite-containing catalyst comes into contact with water vapor at high temperatures, depending on the kinds of zeolite used, degradation due to structural destruction (dealumination from skeleton) tends to proceed, and, since the degradation is so-called permanent degradation where even when regeneration is applied by combusting and removing coke, a recovery cannot be obtained, such a catalyst cannot be used repeatedly.

In a catalytic conversion reaction of high concentration ethylene using a zeolite-containing catalyst, degradation due to deposition of a carbonaceous material on the catalyst, so-called coking degradation is inevitable. When the catalytic conversion reaction is being industrially applied, it is necessary to regenerate and reuse the catalyst by periodically combusting and removing coke deposited on the catalyst. However, when the coke is combusted and removed, water vapor is generated to tend to result in permanent degradation of the catalyst. That is, although combusting deposited coke can recover the activity of the zeolite-containing catalyst degraded by coking, irrecoverable permanent degradation is caused by the regeneration treatment. Such problems that are generated when a catalyst is used while regenerating the catalyst and a method for solving the problems have not been disclosed until now including the patent documents described above.

In view of the above situations, an object of the present invention is to provide, in a method for producing propylene from a hydrocarbon raw material containing ethylene in an amount exceeding 50% by mass under the co-existence of water, a method for producing propylene stably over a long term from ethylene in a high yield and with the reaction/regeneration repeated.

Solution to Problem

The present inventors, after studying hard to solve the problems mentioned above, have found that, when a catalytic conversion reaction of ethylene-containing hydrocarbon is conducted with a zeolite-containing catalyst containing an MFI zeolite having specific compositions and physical properties, even under the co-existence of water, a catalyst is difficult to cause permanent degradation and can be regenerated from degradation due to deposited coke by combusting and removing coke, the permanent degradation of the catalyst due to water vapor generated when the coke is a combusted and removed can be inhibited, and thereby, propylene can be stably produced in a high yield and with activity maintained over the long term, and thereby the present invention was completed.

That is, the present invention is as follows.

[1] A method for producing propylene comprising:
catalytically converting a hydrocarbon raw material containing ethylene in an amount exceeding 50% by mass with a zeolite-containing catalyst while supplying water,
wherein a zeolite contained in the zeolite-containing catalyst satisfies (1) to (3) below;
(1) the zeolite is an MFI zeolite,
(2) a zeolite crystallization index obtained from an X-ray diffraction spectrum is 3.3 or more, and
(3) a molar ratio of silica/alumina ($SiO_2/Al_2O_3$) is 20 to 300.

[2] The method for producing propylene according to [1], wherein water is supplied in an amount of 10% by mass or more based on the hydrocarbon raw material.

[3] The method for producing propylene according to [1] or [2], further comprising:
heat-treating the zeolite-containing catalyst at a temperature equal to or more than 550° C.

[4] The method for producing propylene according to any of [1] to [3], further comprising:
heat-treating the zeolite-containing catalyst at a temperature equal to or more than 300° C. under the presence of water vapor.

[5] The method for producing propylene according to any of [1] to [4], wherein the zeolite-containing catalyst contains at least one kind of metal element selected from the group consisting of elements belonging to group IB in the periodic table.

[6] The method for producing propylene according to any of [1] to [5], further comprising:
combusting coke adhered to the zeolite-containing catalyst.

Advantageous Effects of Invention

According to a producing method of the present invention, even under the co-existence of water, propylene can be produced in a high yield and stably over the long term from a hydrocarbon raw material containing ethylene in an amount exceeding 50% by mass; accordingly, the producing method of the invention is very advantageous when it is industrially conducted.

DESCRIPTION OF EMBODIMENTS

Figure 1:
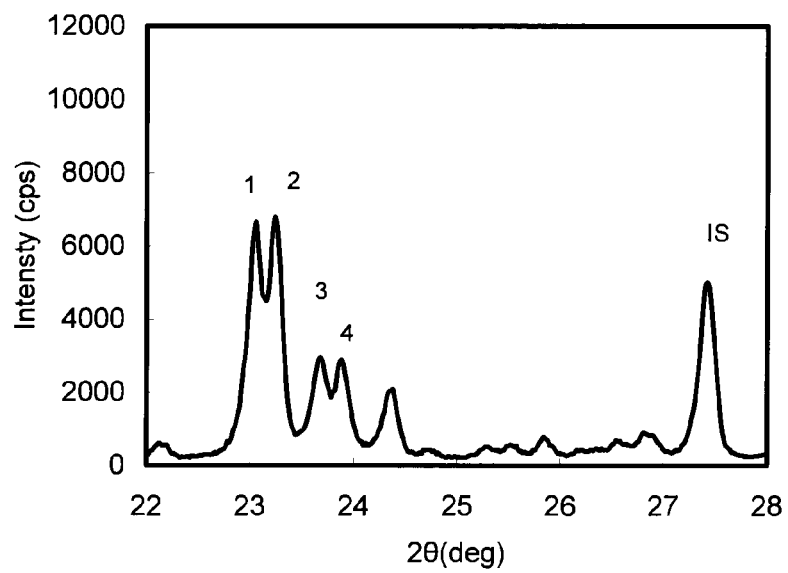
FIG. 1 shows a result of a crystallization index measurement (X-ray diffraction spectrum) of a zeolite used in Example 1.

Hereinafter, the mode (hereinafter abbreviated as "the present embodiment") for carrying out the present invention is described in detail. It is understood that the present invention is not limited to the following embodiment, and can be modified to be implemented within the scope of the gist thereof.

A method according to the present embodiment for producing propylene is a method for producing propylene comprising:
catalytically converting a hydrocarbon raw material containing ethylene in an amount exceeding 50% by mass is with a zeolite-containing catalyst while feeding water,
wherein a zeolite contained in the zeolite-containing catalyst satisfies (1) to (3) shown below;
(1) the zeolite is an MFI zeolite,
(2) a crystallization index of the zeolite obtained from an X-ray diffraction spectrum is 3.3 or more, and
(3) a molar ratio of silica/alumina ($SiO_2/Al_2O_3$) is 20 to 300.

A zeolite contained in a zeolite-containing catalyst of the present embodiment is (1) an MFI zeolite. That is, the zeolite is a zeolite classified as an MFI structure in terms of the framework structure type in conformity with the IUPAC recommendation, and specifically a ZSM-5 zeolite.

When a zeolite contained in a zeolite-containing catalyst is an MFI zeolite, in a catalytic conversion reaction of olefins, high activity and selectivity are exhibited, and high resistance is exhibited to coking degradation. Here, the MFI zeolite is an intermediate pore size zeolite.

(2) A crystallization index of zeolite obtained from an X-ray diffraction spectrum of the zeolite contained in a zeolite-containing catalyst of the present embodiment is 3.3 or more. The crystallization index is preferably 3.5 or more and more preferably 4.0 or more. Here, the crystallization index of zeolite is represented by a ratio of a sum total of peak intensities of four lines between 23 to 24 deg in 2θ, which are characteristic to the MFI zeolite and obtained from an X-ray diffraction spectrum and an intensity of a peak at 2θ=27.4 deg derived from rutile type titania that is an internal reference material added at the time of measurement.

In general, peak intensities of 2θ=23 to 24 deg are taken as an index representing the degree of crystallization of an MFI zeolite (refer to Japanese Patent Laid-Open No. 10-52646). Furthermore, it is also well known to use an internal reference sample and rutile type titania is known to be less in variation in diffraction line intensities due to pulverizing or crushing (refer to X-sen Bunseki no Shinpo 5, H. Sasuga and T. Nakamura, published by Kagaku Gijutsu-Sha (1973), pp. 133-144).

A crystallization index of zeolite obtained from an X-ray diffraction spectrum can be obtained as shown below. Rutile-type titania is measured so as to be 5:1 by mass ratio to dry mass of zeolite and added to a zeolite or a zeolite-containing catalyst described below. The mixed solid is homogeneously pulverized by kneading for 30 min with an automatic mortar. The resulting sample is measured by general X-ray diffractometry in the measurement range of 2θ=20 to 30 deg. From the resulting X-ray diffraction spectrum, a sum total (a) of peak intensities (unit: cps) of four lines at 23.06, 23.22, 23.70 and 23.90 deg characteristic to an MFI zeolite and an intensity (b) of a peak at 27.42 deg derived from rutile type titania are obtained and a crystallization index=(a)/(b) is calculated.

As was mentioned above, peak intensities at 2θ=23 to 24 deg are known to be an index showing a degree of crystallinity of an MFI zeolite. Furthermore, since rutile type titania is adequate as an internal reference sample, irrespective of slight variations of X-ray diffractometers used, tube intensities and measurement conditions, the crystallization index in the present embodiment shows a value intrinsic to a zeolite.

The zeolites, even when these have the same MFI type and the same silica/alumina ratio, when the crystallization indices thereof are different from each other, show different natures. The present inventors have found in a reaction where a hydrocarbon raw material containing ethylene in an amount exceeding 50% by mass is catalytically converted with a zeolite-containing catalyst while supplying water that (1) while, in the case where a crystallization index of a zeolite contained in a zeolite-containing catalyst is less than 3.3, at the same time with degradation of a catalyst owing to deposition of coke, degradation (permanent degradation) due to destruction of a zeolite structure is caused, (2) in the case where a crystallization index of a zeolite contained in a zeolite-containing catalyst is 3.3 or more, although the deposition of coke is caused, the permanent degradation of the catalyst under reaction conditions containing water in a reaction system can be remarkably inhibited from proceeding.

The permanent degradation of catalyst cannot be regenerated by combusting and removing deposited coke; accordingly, the degraded activity of catalyst cannot be recovered. Accordingly, a catalyst prone to be permanently degraded is difficult to repeatedly maintain desired activity. On the other hand, when the activity of a zeolite-containing catalyst is degraded by deposition of coke, activation (regeneration) can be realized by combusting the deposited coke. When coke is deposited on a catalyst containing a zeolite having a crystallization index of 3.3 or more, as was mentioned above, the permanent degradation can be remarkably inhibited; accordingly, by conducting an activation treatment, high activity can be maintained even when the catalyst is repeatedly used.

As an industrial activation treatment, a continuous extraction-continuous regeneration method in a fluidized bed system or a fixed bed swing reactor method can be adopted and, thereby, a high yield can be maintained stably over the long term.

In the Japanese Patent Laid-Open No. 2007-191444, an example where an H-ZSM5 zeolite having a silica/alumina molar ratio of 23.8 is used as a catalyst is described. However, there is no detailed description of the zeolite. Accordingly, a crystallization index of the zeolite is not clear, there is no example where a catalyst is repeatedly used, and resistance to the permanent degradation is neither clear. The inventors tried to confirm a crystallization index of the zeolite. However, it was unsuccessful because the zeolite was not availed commercially and a producing method thereof was neither described. In Japanese Patent Laid-Open No. 2007-191444, a method for producing propylene via a dehydration reaction of ethanol is described. According thereto, even when ethylene is used as a starting raw material, the activity of a catalyst can be evaluated when propylene is continuously produced from ethanol. However, there is no description of the degradation of a catalyst owing to the presence of water in the system. In addition, a zeolite having the crystallization index of 3.3 or more is a substance difficult to generate (in a natural manner) as long as it is intentionally synthesized. By assuming from these facts, the crystallization index of the H-ZSM5 zeolite described in the Japanese Patent Laid-Open No. 2007-191444 can be inferred to be less than 3.3.

(3) A silica/alumina ($SiO_2/Al_2O_3$) molar ratio of a zeolite contained in a zeolite-containing catalyst of the present embodiment is in the range of 20 to 300. The silica/alumina molar ratio of the zeolite is 20 or more from the viewpoint of stable production of the catalyst. On the other hand, when the silica/alumina molar ratio exceeds 300, an ethylene conversion activity is low and, when a high conversion rate is tried to obtain with the catalyst, the propylene selectivity becomes low. In particular, as will be described below, when a step where a heat treatment is conducted at 300° C. or more under the presence of water vapor is conducted as a pretreatment, the activity tends to further decrease.

The silica/alumina molar ratio of zeolite can be measured according to known methods. For example, a zeolite is completely dissolved in an alkali aqueous solution, a resulting solution is analyzed by plasma emission spectroscopy, and thereby the silica/alumina molar ratio can be obtained.

As the zeolite, a metaloaluminosilicate in which part of the aluminum atoms constituting the zeolite framework is replaced with elements such as Ga, Fe, B and Cr and a metalosilicate in which all the aluminum atoms constituting the zeolite framework are replaced with the elements such as those described above can be used. In such a case, the content of the replaced elements in the metaloaluminosilicate or the metalosilicate is converted into the number of moles of alumina, and then the $SiO_2/Al_2O_3$ molar ratio is calculated therefrom.

From the viewpoint of ethylene conversion activity, an acid amount (hereinafter, referred to as a TPD acid amount) obtained from a high-temperature desorption amount in an ammonium temperature-programmed desorption spectrum (TPD) of a zeolite-containing catalyst is preferable to be 50 μmol/g-zeolite or more. A TPD acid amount equal to or more than 50 μmol/g-zeolite can be said relatively high as an acid amount of a zeolite-containing catalyst. In general, when a zeolite-containing catalyst high in the TPD acid amount is used in a reaction for producing propylene with ethylene as a raw material, in addition to that aromatic compounds and paraffin hydrocarbon compounds are much by-produced to tend to lower the propylene yield (selectivity), the activity tends to be remarkably degraded owing to coke generation. By contrast therewith, in the present embodiment, owing to the co-existence of water during a reaction, a decrease in the catalyst activity is gradually (as a cycle of reaction/regeneration is repeated) more moderated owing to influence of water and thereby the selectivity becomes less degraded. On the other hand, although the co-existence of water influences the permanent degradation of the catalyst, by setting a crystallization index of the zeolite at 3.3 or more, the degradation can be made remarkably slower in progress (further slower as the activity is degraded). That is, a problem of activity degradation caused by coke generation is solved by the co-existence of water, and a problem of permanent degradation caused by the co-existence of the water can be solved by making a crystallization index of zeolite larger; accordingly, the propylene yield can be maintained over the long term. Even when the coking degradation is suppressed by the co-existence of water, in the case where a crystallization index of zeolite of a catalyst is 3.3 or less, the permanent degradation proceeds at a speed comparable to the coking degradation to result in remarkable degradation in an activity activation rate after coke removal; accordingly, high activity cannot be maintained.

The TPD acid amount of the present embodiment is a quantity as measured in the following manner.

A catalyst as a sample is placed in a measurement cell in a temperature-programmed desorption spectrometer, the air in the measurement cell is replaced with helium gas, the temperature inside the cell is stabilized at 100° C., thereafter the interior of the cell is once subjected to a vacuum treatment, and successively ammonia gas is fed to the cell up to a pressure of 100 Torr. This condition is maintained for 30 minutes, ammonia is adsorbed to the catalyst. Thereafter, the interior of the cell is again evacuated to vacuum to let out the ammonia gas not absorbed to the catalyst, and the carrier gas is changed over to helium gas to bring the interior of the cell back to atmospheric pressure. Then, the measurement cell is connected to a quadrupole mass spectrometer, the pressure inside the cell is set at 200 Torr, and while the interior of the cell is being increased up to 600° C. in temperature at a temperature increase rate of 8.33° C./min, the ammonia desorbed from the catalyst is detected. The pressure of the interior of the cell during the desorption is controlled so as to be maintained at approximately 200 Torr.

The obtained temperature-programmed desorption spectrum is divided by means of the waveform separation based on the Gaussian distribution, the desorption amount of ammonia is determined from the sum of the areas of the waveforms each having a peak top at a desorption temperature of 240° C. or higher, and the TPD acid amount is represented by the value (unit is µmol/g-zeolite) obtained by dividing the desorption amount of ammonia by the mass of the zeolite contained in the catalyst. "240° C." is an indicator to be used exclusively for identification of the peak top position, but dose not mean to restrict the area calculation to the portions falling in the range of 240° C. or higher. As long as a waveform has a peak top at 240° C. or higher, the calculation of "the area of the waveform" includes the total area inclusive of the portion falling in the range of 240° C. or lower. When two or more waveforms each have a peak top at 240° C. or higher, the concerned area is defined as the sum of the areas of such individual waveforms.

A synthesis method of the above-mentioned MFI zeolite having a specific physical property and a composition is not particularly restricted. However, the MFI zeolite can be produced by optimizing various kinds of conditions of so-far known hydrothermal synthesis methods of MFI zeolites.

As means for obtaining an MFI zeolite efficiently by a hydrothermal synthesis method, there are a method where a hydrothermal synthesis is conducted with ammonium salts, urea compounds, amines or alcohols as an adequate organic molding agent (structure-directing agent=SDA) and a method where a hydrothermal synthesis is conducted with an MFI zeolite obtained by hydrothermal synthesis added as a seed crystal or a seed slurry in a crystal stage. Furthermore, not only organic SDAs but also inorganic positive ions or negative ions are known to be relevant to a structure, that is, a zeolite synthesis depends on complicated workings of the respective components. In the hydrothermal synthesis methods such as mentioned above of MFI zeolite, when the kinds of raw materials and additives (SDA), addition amounts, pH, silica/alumina molar ratio, a medium, a raw material charging composition such as an existence ratio of positive ions and negative ions, synthesis conditions such as a synthesis temperature and a synthesis time are appropriately optimized, an MFI zeolite having a crystallization index of the present embodiment can be synthesized.

Specifically, a method where a seed slurry described in, for example, Japanese Patent Laid-Open No. 10-52646 is used to synthesize and a method where a synthesis is conducted with silicate esters described in WO/064560 as a silica source under the co-existence of alcohol and a tetrapropyl ammonium salt (an aluminum source is necessary to be appropriately added so as to be a desired silica/alumina molar ratio of a zeolite used in the present embodiment) can be cited.

Furthermore, as long as an MFI zeolite has the above-mentioned specific physical property and composition, commercially available products can be used. For example, such as MFI-27 (trade name, manufactured by SudChemie AG and ZD03030 (MFI-42) (trade name, manufactured by Zeolyst International Company) can be cited.

A zeolite-containing catalyst of the present embodiment can be produced by molding, for example, as shown below, a zeolite having the above-mentioned specific physical property and composition.

The molding method is not particularly restricted and a general method can be used. Specifically, a method where catalyst components are compression molded, an extrusion molding method and a spray dry molding method most appropriate for a fluidized bed reaction method can be cited. Furthermore, a binder can be used at molding. The binder is not particularly restricted. For example, silica, alumina and kaolin can be used singularly or in a combination thereof. As the binders, commercially available products can be used. A mass ratio of zeolite/binder is preferably in the range of 10/90 to 90/10 and more preferably in the range of 20/80 to 80/20.

The zeolite-containing catalyst of the present embodiment may contain at least one metal element selected from the group consisting of the elements belonging to the group IB in the periodic table. This means that the zeolite in the concerned catalyst contains or supports the group IB metal(s) as the state(s) of the corresponding cation(s). It is a preferable mode that the zeolite-containing catalyst contains at least one metal selected from the group consisting of the metals belonging to the group IB in the periodic table, namely, copper, silver and gold. Among the group IB metals, copper and silver are preferable, and silver is more preferable. It is to be noted that the term "periodic table" in the present embodiment means the periodic table described in CRC Handbook of Chemistry and Physics, 75th edition, by David R. Lide et al., published by CRC Press Inc., (1994-1995), pp. 1 to 15.

At least part of the ion exchange sites of the zeolite contained in the zeolite-containing catalyst are preferably exchanged with the group IB metal cations and/or protons. Additionally, the ion exchange sites other than those exchanged with the group IB metal cations and/or protons may be exchanged with alkali metal cations, alkali earth metal cations and other metal cations.

Examples of a method in which at least one metal element selected from the group consisting of the metal elements belonging to the group IB in the periodic table is made to be contained in the zeolite-containing catalyst include a method in which a group IB metal element is made to be contained in the zeolite, in particular, for example, a method in which a zeolite or a zeolite-containing catalyst containing no group IB metal is treated with an ion exchange method, and more specifically, a liquid phase ion exchange method and a method in which an impregnation supported catalyst is treated at high temperatures to be thereby subjected to a solid phase ion exchange treatment.

In the case where a group IB metal is made to be contained in a zeolite or a zeolite-containing catalyst, it is necessary to use a salt of the group IB metal. Examples of such a salt of the group IB metal include silver nitrate, silver acetate, silver sulfate, copper chloride, copper sulfate, copper nitrate and gold chloride. Among these preferably used are silver nitrate and copper nitrate, and more preferably used is silver nitrate. The content of the group IB metal in the zeolite is preferably 0.1 to 5% by mass and more preferably 0.2 to 3% by mass. Here, the content of the group IB metal in the zeolite can be determined by means of a method such as X-ray fluorescence analysis.

Before a zeolite-containing catalyst is brought into contact with a hydrocarbon raw material, the zeolite-containing catalyst may be subjected to a pre-treatment.

As a preferable pre-treatment step, (A) a step where a heat treatment is conducted at a temperature equal to or more than 550° C., and (B) a step where a heat treatment is conducted at a temperature equal to or more than 300° C. under the presence of water vapor can be cited. When the pre-treatments are conducted, a catalyst tends to be more remarkable in suppressing degradation and in improving the selectivity.

In the case of a method of the (A), it is desirable to treat at a temperature of 550° C. or more and 1000° C. or less under the flow of air or an inert gas such as nitrogen (although an atmosphere is not particularly restricted).

In the case of a method of the (B), it is desirable to treat at a temperature of 300° C. or more and 900° C. or less by flowing a mixed gas of air or an inert gas such as nitrogen and steam (water vapor) (although an atmosphere is not particularly restricted) under the condition of water vapor partial pressure of 0.01 atmosphere or more. In the present specification, the (B) step is simply referred to as "water vapor treatment" in some cases.

In a producing method of the present embodiment, water coexists in a reaction system; accordingly, a state the same as that subjected to a water vapor treatment in a heated state in a reaction system or a state nearly the same as that is realized. Accordingly, without conducting, in advance of a reaction, (A) a heat treatment at a temperature equal to or more than 550° C. and/or (B) a water vapor treatment, that is, a pre-treatment, when the zeolite-containing catalyst is supplied to a reaction and the deposited coke is combusted and removed to regenerate, that is, when a cycle of reaction/regeneration is repeated, the zeolite-containing catalyst gradually approaches a catalyst property obtained when the pre-treatment is conducted. In other words, the pre-treatment can be said a method capable of obtaining a temporal selectivity improvement effect of a catalyst of the present embodiment by shortening a time. At this time, in a zeolite of the present embodiment where a crystallization index is 3.3 or more, a decrease in the activity in the pre-treatment (furthermore, even when a cycle of reaction/regeneration is repeated) is small as mentioned above.

A hydrocarbon raw material contains ethylene in an amount exceeding 50% by mass. The ethylene content in a hydrocarbon raw material is preferably 55% by mass or more and more preferably 60% by mass or more. When the ethylene content is 50% by mass or less like in the conventional technology, since there is necessity of mixing a diluting gas in a hydrocarbon raw material in some cases, the productivity tends to decrease unfavorably.

As the ethylene-containing hydrocarbon raw material, there can be used a material obtained, for example, by thermal decomposition and/or oxidative dehydrogenation reaction of ethylene, or by dehydration reaction of ethanol. Needless to say, ethanol may be derived from biomass.

The hydrocarbon raw material may contain alkanes, other olefins and the like. Examples of the alkanes include methane, ethane, propane, butane, pentane, hexane, heptane, octane and nonane. Additionally, examples of the olefins include propylene, butene, pentene, hexene, heptene, octene and nonene. In addition to those described above, the ethylene-containing hydrocarbon raw material may also contain: cycloalkanes such as cyclopentane, methylcyclopentane and cyclohexane; cycloolefins such as cyclopentene, methylcyclopentene and cyclohexene; and/or dienes such as cyclohexadiene, butadiene, pentadiene and cyclopentadiene and acetylenes such as acetylene, and methylacetylene. Further, the ethylene-containing hydrocarbon raw material may also contain oxygen-containing compounds such as t-butyl alcohol, methyl t-butyl ether, diethyl ether, methyl ethyl ether, dimethyl ether, ethanol and methanol.

The ethylene-containing hydrocarbon raw material may also contain, hydrogen, nitrogen, carbon dioxide, carbon monoxide and the like.

The reaction product produced by a so-called steam cracking method of ethane in which ethane is thermally decomposed in the presence of water vapor contains, in addition to ethylene, unreacted ethane, hydrocarbons such as acetylene, water, hydrogen, carbon dioxide and carbon monoxide; however, the reaction product can be used, as it is, as a raw material.

A biomass ethanol is not particularly limited as long as the biomass ethanol is an ethanol derived from plant resources. Specific examples of biomass ethanol include the ethanols obtained by fermentation of sugarcane and corn, and the ethanol obtained from wood resources such as waste wood, thinned wood, rice straw and agricultural products.

Propylene is separated by means of a technique such as distillation separation from the reaction product (propylene-containing gas) produced by bringing the hydrocarbon raw material into contact with the zeolite-containing catalyst, and at least part of the rest can be recycled to the reactor. The residue obtained by removing propylene from the reaction product contains an ethylene-containing low boiling point component and/or a butene-containing high boiling point component. In this case, the content of ethylene in the mixed raw material composed of the recycled component and the feedstock is a concentration exceeding 50% by mass.

A zeolite-containing catalyst containing a zeolite, which is used in the present embodiment and has specific physical property and composition is difficult to cause permanent degradation even when water is present in a reaction system. Accordingly, since reaction products generated by a so-called steam cracking method where ethane that is recently gathering attention as a raw material of a new propylene producing reaction is pyrolyzed under the presence of water vapor can be used as they are or biomass ethanol (ethylene and water are generated by dehydration) can be used as it is, the zeolite-containing catalyst of the embodiment can be industrially used very advantageously.

A method of the present embodiment for producing propylene includes a step of catalytic conversion where a hydrocarbon raw material containing ethylene in an amount of exceeding 50% by mass is brought into contact with a zeolite-containing catalyst containing the specific zeolite with water supplied.

Here, the "catalytic conversion" means a contact reaction that proceeds at an interface of an inhomogeneous phase, that is, a reaction where a reaction raw material in gaseous phase and/or liquid phase is brought into contact with a solid catalyst, and a reaction where a raw material is converted by contact (conversion of substance). In the case of catalytic conversion of ethylene, when a raw material containing ethylene is supplied into a reactor incorporating a zeolite-containing catalyst, the raw material comes into contact with the catalyst, and thereby at least part of ethylene contained in the raw material is catalytically converted to generate propylene.

In a method of the present embodiment for producing propylene, a reaction is conducted with a hydrocarbon raw material containing ethylene and water supplied to a reactor. The co-existence of water is known to be effective, by improving the reaction selectivity and by suppressing coke generation, in extending a lifetime of a catalyst and is also effective, by diluting a hydrocarbon raw material, in decreasing ethylene partial pressure in a reaction system. A decrease in olefin partial pressure is advantageous in improving a yield of propylene due to a reaction equilibrium. However, when partial pressure of water in a reaction system is high, there is a concern of acceleration of the permanent degradation owing to structural destruction of the zeolite. Accordingly, a supply amount of water in a reactor is, based on a hydrocarbon raw material, preferably 10% by mass or more, more preferably 20% by mass or more and still more preferably 30 to 80% by mass from the viewpoint of the reaction result, coke suppression effect, productivity and permanent degradation suppression.

In order to supply water into a reactor, other than a supply path of a hydrocarbon raw material, separately, a supply path of water may be disposed, or a hydrocarbon raw material containing water may be supplied. As was mentioned above, reaction products obtained by steam cracking of ethane contain water as a raw material and, when ethanol is used as a raw material, ethylene and water are generated by dehydration; accordingly, there is no need of separately supplying water.

The production of propylene based on the catalytic conversion reaction of ethylene is an equilibrium reaction, and the maximum yield of propylene is attained in the vicinity of the conversion ratio of ethylene of 70% in the equilibrium. Accordingly, for the purpose of efficiently obtaining propylene, the conversion ratio of ethylene preferably falls within a range from 45 to 85% and more preferably within a range from 50 to 80%. It is to be noted herein that the conversion ratio of ethylene is calculated on the basis of the following calculation formula (1).

Conversion ratio of ethylene=(ethylene concentration in the feeding flow at the reactor inlet−ethylene concentration in the discharging flow at the reactor outlet)/(ethylene concentration in the feeding flow at the reactor inlet)×100    [Formula (1)]

There is a thermal equilibrium of generated olefins; accordingly, from the viewpoint of obtaining propylene in a high yield, as a reaction temperature, a high temperature exceeding 500° C. is adequate. A reaction temperature is preferably in the range of 520° C. to 600° C. from the viewpoint of suppressing aromatization and acceleration of coking degradation at higher temperatures. It is usual that, under high temperature reaction conditions, when water coexists in a reaction system, a catalyst is accelerated in degradation. However, when a crystallization index of zeolite is 3.3 or more, even under high temperatures, degradation caused by co-existence of water can be suppressed; accordingly, a high yield can be maintained over the long term. The reaction pressure preferably falls within a range from 0.1 to 30 atm and more preferably within a range from 0.5 to 10 atm.

The feeding rate of the hydrocarbon raw material is preferably 0.1 to 20 $Hr^{-1}$ and more preferably 0.5 to 10 $Hr^{-1}$, in terms of the mass hourly space velocity (WHSV) with reference to the mass of the zeolite in the zeolite-containing catalyst.

No particular constraint is imposed on the reactor in which the ethylene-containing hydrocarbon raw material is made to react by being brought into contact with the zeolite-containing catalyst; as the reactor, any of a fixed bed reactor, a fluid bed reactor, a moving bed reactor and the like can be utilized.

When a zeolite-containing catalyst is used in a production reaction of propylene, carbonaceous compounds (coke) are gradually generated on the catalyst and thereby the catalytic activity decreases in some cases. In that case, when a fixed bed reactor is used in the production reaction of propylene, the hydrocarbon raw material supply is temporarily halted, and the coke accumulated on the zeolite-containing catalyst is combusted with an oxygen-containing gas and thus the zeolite-containing catalyst can be regenerated. Additionally, when a moving bed reactor or a fluidized bed reactor is used, part of the zeolite-containing catalyst is continuously or intermittently taken out from the reactor, the coke deposited on the zeolite-containing catalyst is combusted with an oxygen-containing gas and thus the regeneration of the zeolite-containing catalyst can be conducted. The zeolite-containing catalyst after regeneration can be returned to the reactor. The regeneration of the zeolite-containing catalyst is usually conducted in air or a mixed gas composed of air and an inert gas under the condition of 400 to 700° C.

EXAMPLES

Hereinafter, the present embodiment is described more specifically with reference to Examples, but the present embodiment is not limited only to these Examples.

It is to be noted herein that the measurement methods adopted in Examples and Comparative Examples are as follows.

(1) Measurement of the Silica/Alumina ($SiO_2/Al_2O_3$) Molar Ratio of Zeolite

To 50 g of a 5 N aqueous solution of sodium hydroxide (NaOH), 0.2 g of zeolite was added. The mixture thus obtained was transferred into a stainless steel microbomb with an inner tube made of Teflon (trade mark), and the microbomb was sealed. The microbomb was retained in an oil bath for 15 to 70 hours to completely dissolve the zeolite. The obtained zeolite solution was diluted with ion-exchanged water, and the concentrations of the silicon and the aluminum in the diluted solution were measured with a plasma emission spectrometer (ICP apparatus) described below, and from the measurement results, the silica/alumina molar ratio of the zeolite was calculated.

Apparatus: JOHBIN YVON (JY138 ULTRACE) manufactured by Rigaku Denki Co., Ltd.

Measurement Conditions

Silicon measurement wavelength: 251.60 nm

Aluminum measurement wavelength: 396.152 nm

Plasma power: 1.0 kW

Nebulizer gas: 0.28 L/min

Sheath gas: 0.3 to 0.8 L/min

Coolant gas: 13 L/min (2) Measurement of X-ray Diffraction of Zeolite

To 5 g of a zeolite (In the case of a molded body, an amount of a zeolite contained therein is set at 5 g.), 1 g of pulverized rutile type titania was added, followed by kneading with an electrically-driven mortar for 30 min. The resulting powder sample was subjected to X-ray diffraction measurement under the following conditions.

Apparatus: MXP-18 (trade name, manufactured by MacScience)

| Measurement conditions: | |
|---|---|
| Radiation source: | Cu (measured with Kα line) |
| Tube voltage: | 40.0 KV |
| Tube current: | 190.0 mA |
| Data range: | 20 to 30 deg |
| Sampling interval: | 0.02 deg |
| Scanning speed: | 2.00 deg/min |
| Dispersion slit: | 1.00 deg |
| Scattering slit: | 1.00 deg |
| Light receiving slit: | 0.15 mm |

From the resulting X-ray diffraction spectrum, a sum total (a) of peak intensities (unit: cps) of four lines at 23.06, 23.22, 23.70 and 23.90 deg, which are peaks characteristic to an MFI zeolite, and a peak intensity (b) at 27.42 deg derived from rutile type titania were obtained, and, from the ratio (a)/(b), a crystallization index was obtained.

(3) Measurement of the TPD Acid Amount

The measurement was conducted by using an automatic temperature-programmed desorption spectrometer, TPD-1-Atw, manufactured by BEL Japan, Inc. in the following manner.

In a special glass cell, 100 mg of a catalyst sample was filled (when the sample is a molded body, the sample was made powdery to be filled in). While helium as the carrier gas was being fed to the cell at a flow rate of 50 cc/min, the sample was heated up to 500° C. and subjected to a heat treatment for 1 hour as a preliminary treatment, and then the sample temperature was set at 100° C. After the sample temperature was stabilized at 100° C., the interior of the cell was subjected to a vacuum treatment (0.01 Torr). Successively, ammonia gas was fed to the interior of the cell, and the pressure inside the cell was set at 100 Torr. The sample was maintained under such condition for 30 minutes so as for ammonia to be adsorbed to the catalyst. Thereafter, the interior of the cell was again subjected to a vacuum treatment to remove the unadsorbed ammonia. The carrier gas was changed over to helium, the interior of the cell was brought back to atmospheric pressure. Then, the pressure inside the cell was set so as to be maintained at 200 Torr, and while the temperature was being increased up to 600° C. at a temperature increase rate of 8.33° C./min, the desorbed ammonia was detected with a quadrupole mass spectrometer, manufactured by ANELVA Corp., connected to the cell.

The obtained temperature-programmed desorption spectrum was divided by means of the waveform separation based on the Gaussian distribution, by using a waveform analysis software "WaveAnalysis" manufactured by BEL Japan, Inc.

On the basis of the results of the waveform separation analysis, the desorption amount of ammonia was determined from the sum of the areas of the waveforms each having a peak top at a desorption temperature of 240° C. or higher, with reference to a separately determined calibration curve, and the obtained desorption amount of ammonia was converted to a value represented in terms of the quantity per unit mass of zeolite (unit: μmol/g-zeolite).

(4) Analysis of Reaction Products

Reaction products were analyzed by gas chromatography (GC) with an apparatus and under the conditions shown below.

Apparatus: GC-17A (trade name, manufactured by Shimadzu Corporation)

Column: Custom Capillary Column SPB-1 (trade name, manufactured by SUPELCO Co., Ltd., the U.S., inner diameter: 0.25 mm, length: 60 m, film thickness: 3.0 μm)

Sample gas amount: 1 mL (a sampling line was kept at 200 to 300° C. by heating)

Temperature increase program: The temperature was kept for 12 min at 40° C., followed by elevating at 5° C./min up to 200° C., further followed by keeping at 200° C. for 22 min.

Split ratio: 200:1

Carrier gas (nitrogen) flow rate: 120 mL/min

FID detector: air feeding pressure: 50 kPa (approximately 500 mL/min); hydrogen feeding pressure: 60 kPa (approximately 50 mL/min)

Measurement method: A TCD detector and an FID detector were connected in series, hydrogen and hydrocarbons having one and two carbon atoms were detected with the TCD detector and hydrocarbons having three or more carbon atoms were detected with the FID detector. At 10 min after the start of analysis, the detection output was switched from TCD to FID.

Example 1

[Hydrothermal Synthesis of Raw Material Zeolite]

To 92 kg of #3 Sodium Silicate (trade name, manufactured by Fuji-kagaku K.K., $SiO_2$: 25% by mass, $Na_2O$: 8% by mass), 95 kg of water and 7.3 kg of aluminum sulfate hexadecahydrate, and 3.0 kg of sulfuric acid (purity: 97%), and a solution obtained by dissolving 1.15 kg of 1,3-dimethyl urea in 150 kg of water were added under stirring, and thereby a homogeneous gel was obtained. The gel was charged in a 600 L autoclave, a hydrothermal synthesis was conducted at 160° C. for 30 hours under stirring, and thereby a Na-type ZSM-5 zeolite slurry was obtained. The slurry was repeatedly subjected to filtering and washing with water until pH of the filtrate became 8 or less, followed by drying at 120° C. for 20 hours, further followed by calcining in air at 550° C. for 3 hours, and thereby a powder of Na-type ZSM-5 zeolite was obtained.

To 92 kg of #3 Sodium Silicate, 245 kg of water and 7.3 kg of aluminum sulfate hexadecahydrate, and 3.8 kg of sulfuric acid (purity: 97%), and 3.0 kg of the resulting powder of Na-type ZSM-5 zeolite were added, and thereby a homogeneous gel was obtained. The gel was charged in a 600 L autoclave, a hydrothermal synthesis was conducted at 150° C. for 10 hours under stirring, and thereby a seed slurry was obtained.

In the next place, to 92 kg of #3 Sodium Silicate, 245 kg of water and 3.5 kg of aluminum sulfate hexadecahydrate, and 4.9 kg of sulfuric acid (purity: 97%), and 167 kg of the resulting seed slurry were added, and thereby a homogeneous gel was obtained. The gel was charged in a 600 L autoclave and hydrothermal synthesis was conducted at 160° C. for 45 hours under stirring to crystallize.

The resulting slurry was washed with water while filtering by centrifugation until pH became 9 or less, followed by drying at 120° C. for 20 hours, further followed by calcining in air at 550° C. for 3 hours, and thereby a powder of Na-type ZSM-5 zeolite was obtained. Furthermore, the dried material was made a 10% by mass slurry in a 1 N nitric acid aqueous solution and ion-exchanged at room temperature for 3 hours, followed by washing with water while filtering by centrifugation until pH became 4.5 or more, still further followed by drying at 120° C. for 20 hours, and thereby a powder of an H-type ZSM-5 zeolite was obtained.

To 5 g of the resulting H-type ZSM-5 zeolite, 1 g of rutile type titania was added, followed by kneading with an electrically-driven mortar for 30 min, and an X-ray diffraction spectrum of the resulting sample is shown in FIG. 1. From the results of X-ray diffraction measurement, a crystallization index of the H-type ZSM-5 zeolite was obtained as 3.73. Furthermore, a silica/alumina molar ratio thereof was 40.

[Preparation of Zeolite-containing Catalyst]

The resulting H-type ZSM-5 zeolite was kneaded with silica sol, followed by extrusion molding. The content of zeolite was 50% by mass. The resulting extrusion-molded catalyst was dried at 120° C. for 6 hours, followed by calcining at 700° C. for 2 hours, and thereby a columnar zeolite-containing molded catalyst having a diameter of 2 mm and a length of 3 to 5 mm was obtained. The resulting molded catalyst was ion-exchanged by stirring in a 0.5 N nitric acid aqueous solution, followed by washing with water, further followed by drying at 120° C. for 5 hours.

[Production of Propylene]

In Examples 1 to 4, for the purpose of comparing the activity of a catalyst over time and a degradation behavior thereof, catalysts were water vapor-treated in advance and used in production reactions of propylene, and reaction results were evaluated.

In a stainless reaction tube having an inner diameter φ of 21.2 mm, 60 g of the resulting zeolite-containing molded catalyst was charged, and a water vapor treatment was conducted for 5 hours under the conditions of a temperature of 650° C., a steam flow rate of 107 g/hr, and a nitrogen flow rate of 200 NL/hr. A TPD acid amount of a water vapor-treated catalyst was measured and found to be 87 μmol/g-zeolite.

In a stainless reaction tube having an inner diameter φ of 21.2 mm, 50 g of the resulting water vapor-treated catalyst was charged and a reaction was conducted under the following conditions.

Raw material feeding rates: ethylene 50.77 NL/hr (flow rate based on standard conditions)
:hydrogen 50.45 NL/hr
:nitrogen 27.29 NL/hr
:water 31.75 g/hr
Reaction pressure: 0.14 MPa/G
Reaction temperature: 550° C.

A reaction product at 2 hours after the start of feeding the raw materials was introduced from a reactor outlet directly in a gas chromatography unit (TCD, FID detectors) to analyze a composition.

Thereafter, while appropriately analyzing a reaction product, a reaction was conducted continuously for 24 hours.

Figure 2:
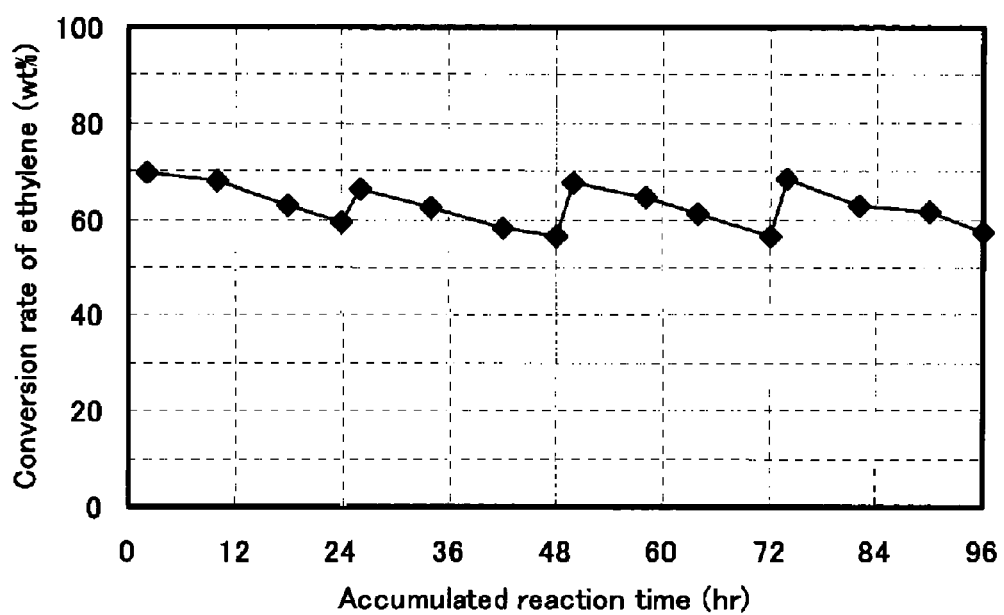
FIG. 2 shows a result of a reaction/regeneration repeating test in Example 1.

After a reaction was conducted for 24 hours, feeding of ethylene, hydrogen and water was stopped, while nitrogen gas was fed at 480 NL/hr, a temperature of a catalyst layer was set at 480° C. Thereafter, air feeding was started at 24 NL/hr and thereby coke deposited on the catalyst was combusted and removed (regeneration step). An oxygen concentration of an inlet gas at the time of start was 1%. While monitoring CO and $CO_2$ concentrations in a gas at a reactor outlet by GC, catalyst regeneration (combustion and removal of deposited coke) was completed under the conditions shown below.
(1) Temperature: 480° C., oxygen concentration: 1%, 1 hour
(2) Temperature: 520° C., oxygen concentration: 1%, 3 hours
(3) Temperature: 550° C., oxygen concentration: 1%, 3 hours
(4) Temperature: 550° C., oxygen concentration: 5%, 1 hour
(5) Temperature: 580° C., oxygen concentration: 5%, 2 hours According to a method described above, with one cycle of a 24 hours reaction and a 10 hours regeneration, 4 cycles were repeated. The test results are shown in Table 1 and FIG. 2.

Example 2

The zeolite obtained in Example 1 was used to prepare, mold and pre-treat a catalyst in a manner similar to Example 1. A TPD acid amount of the resulting water vapor-treated zeolite-containing catalyst was measured and found to be 89 μmol/g-zeolite.

A reaction evaluation test was conducted in a manner similar to Example 1 except that 50 g of the resulting water vapor-treated catalyst was charged in a stainless reaction tube having an inner diameter φ of 21.2 mm, and a test was conducted by repeating three cycles at reaction temperatures for the first and third reactions set at 520° C. and at a reaction temperature for the second reaction set at 580° C. The test results are shown in Table 2.

From the test results, it was found that, a propylene yield tended to decrease a little at low temperatures from the restriction of olefins equilibrium, and coking degradation is accelerated at 580° C. However, even under such a high temperature as 580° C., degradation owing to the co-existence of water was suppressed.

Example 3

An $NH_4$-type MFI zeolite ZD03030 (silica/alumina molar ratio: 42) manufactured by Zeolyst International Company was kneaded with silica sol and molded by extrusion. The content of zeolite was 50% by mass. The resulting extrusion-molded catalyst was dried at 120° C. for 6 hours and calcined at 700° C. for 2 hours and thereby a columnar zeolite-containing molded catalyst having a diameter of 2 mm and a length of 3 to 5 mm was obtained. The resulting molded catalyst was ion-exchanged by stirring in a 0.5 N nitric acid aqueous solution, followed by washing with water, further followed by drying at 120° C. for 5 hours.

Figure 3:
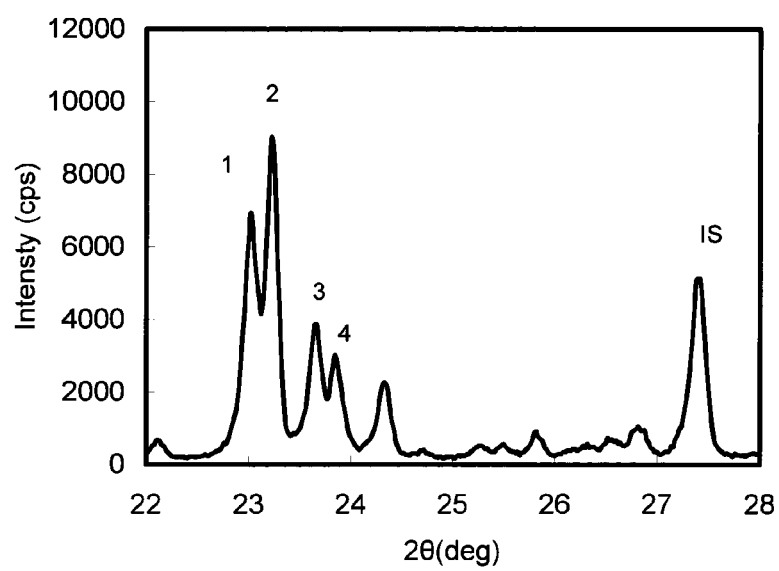
FIG. 3 shows a result of a crystallization index measurement (X-ray diffraction spectrum) of a zeolite used in Example 3.

By contrast, a crystallization index of the zeolite was 4.45. An X-ray diffraction spectrum is shown in FIG. 3.

[Production of Propylene]

In a stainless reaction tube having an inner diameter φ of 21.2 mm, 60 g of the resulting zeolite-containing molded catalyst was charged, and a water vapor treatment was conducted for 5 hours under the conditions of temperature of 650° C., steam flow rate of 107 g/hr, and nitrogen flow rate of 200 NL/hr. A TPD acid amount of a water vapor-treated catalyst was measured and found to be 92 μmol/g-zeolite.

Figure 4:
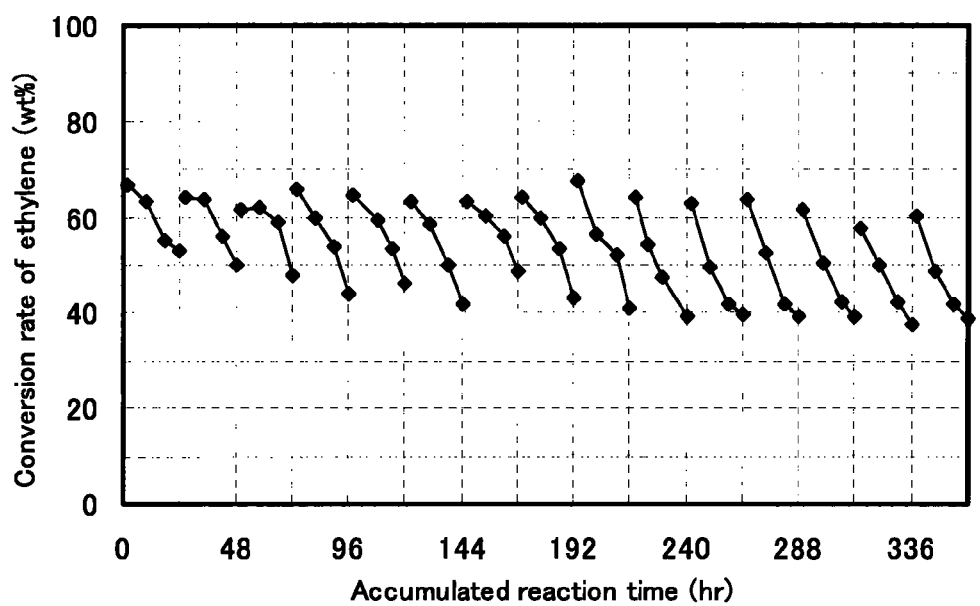
FIG. 4 shows a result of a reaction/regeneration repeating test in Example 3.

In a stainless reaction tube having an inner diameter φ of 21.2 mm, 50 g of the resulting water vapor-treated catalyst was charged and a reaction/regeneration repeating test was conducted 15 cycles under the conditions similar to Example 1. The test results are shown in FIG. 4.

Example 4

H-MFI type zeolite MFI-27 (silica/alumina molar ratio: 27) manufactured by SudChemie AG was kneaded with silica sol, followed by extrusion molding. The content of zeolite was 50% by mass. The resulting extrusion-molded catalyst was dried at 120° C. for 6 hours, followed by calcining at 700° C. for 2 hours, and thereby a columnar zeolite-containing molded catalyst having a diameter of 2 mm and a length of 3 to 5 mm was obtained. The resulting molded catalyst was ion-exchanged by stirring in a 0.5 N nitric acid aqueous solution, followed by washing with water, further followed by drying at 120° C. for 5 hours.

Figure 5:
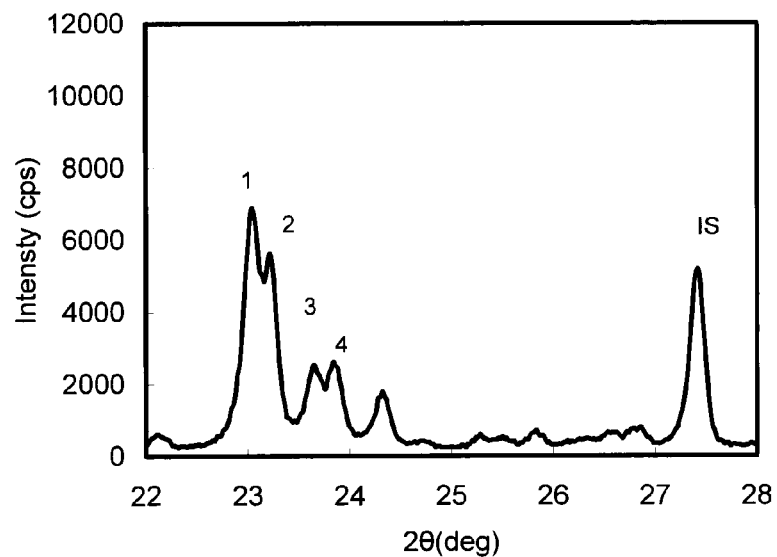
FIG. 5 shows a result of a crystallization index measurement (X-ray diffraction spectrum) of a zeolite used in Example 4.

By contrast, a crystallization index of the zeolite was 3.37. An X-ray diffraction spectrum is shown in FIG. 5.

[Production of Propylene]

Figure 6:
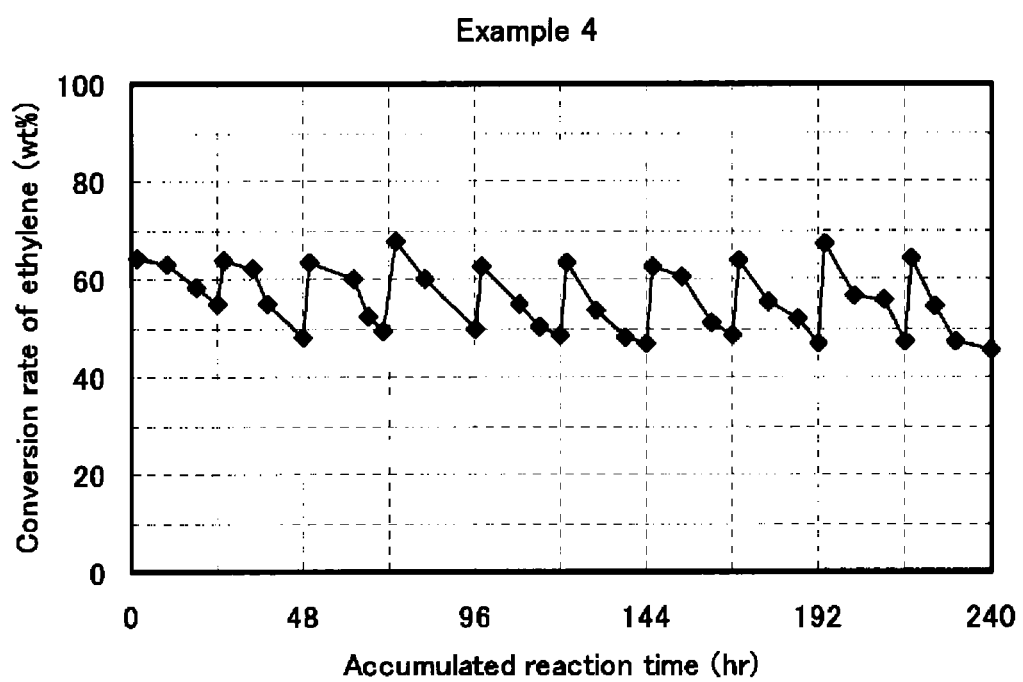
FIG. 6 shows a result of a reaction/regeneration repeating test in Example 4.

In a stainless reaction tube having an inner diameter φ of 21.2 mm, 60 g of the resulting zeolite-containing molded catalyst was charged, and a water vapor treatment was conducted for 5 hours under the conditions of a temperature of 650° C., a steam flow rate of 107 g/hr, and a nitrogen flow rate of 200 NL/hr. A TPD acid amount of a water vapor-treated catalyst was measured and found to be 88 μmol/g-zeolite. In a stainless reaction tube having an inner diameter φ of 21.2 mm, 50 g of the resulting water vapor-treated catalyst was charged, and a reaction/regeneration repeating test was conducted 10 cycles under the conditions similar to Example 1. The test results are shown in FIG. 6.

Example 5

Silver exchange was applied to the zeolite-containing molded catalyst obtained in Example 1. In 450 g of a 0.1 N silver nitrate aqueous solution, 50 g of the zeolite-containing molded catalyst was added, followed by stirring for 2 hours at room temperature, further followed by filtering and washing with water, still further followed by drying the zeolite-containing molded catalyst at 120° C. for 5 hours, and thereby a silver-supporting type zeolite-containing molded catalyst was obtained. A silver-supporting amount was measured by fluorescent X-ray analysis and found to be 0.95% by mass.

In a stainless reaction tube having an inner diameter φ of 21.2 mm, 50 g of the resulting silver-supporting type zeolite-containing molded catalyst was charged, and a water vapor treatment was conducted for 5 hours under the conditions of a temperature of 650° C., a steam flow rate of 107 g/hr, and a nitrogen flow rate of 200 NL/hr. A TPD acid amount of a water vapor-treated catalyst was measured and found to be 102 μmol/g-zeolite.

Figure 7:
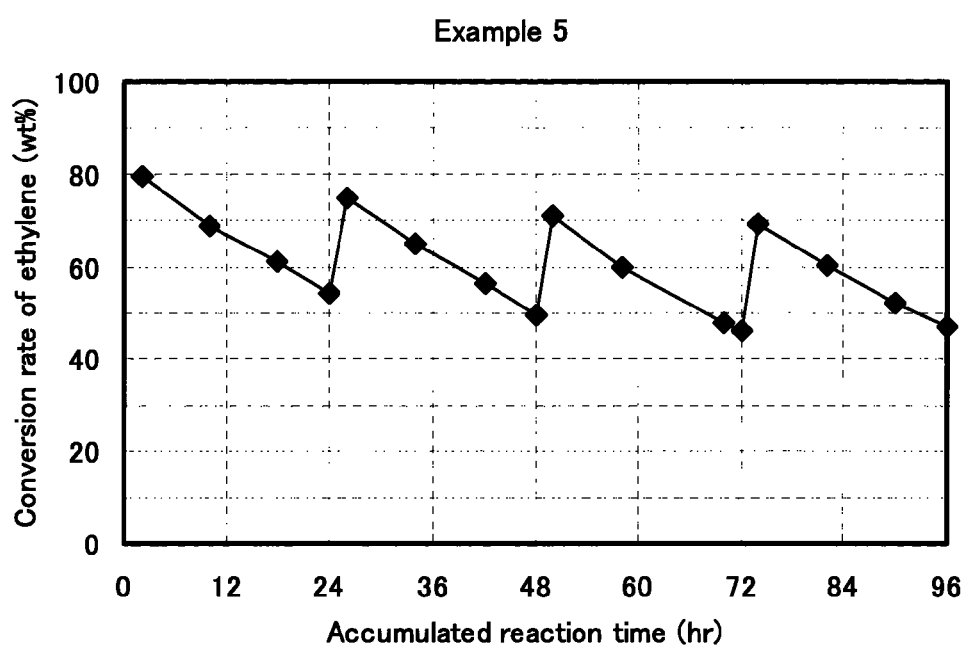
FIG. 7 shows a result of a reaction/regeneration repeating test in Example 5.

Four cycles of the reaction/regeneration repeating test were conducted according to a method similar to Example 1 except that a reaction was conducted with a charging amount of the water vapor-treated silver-supporting type zeolite-containing molded catalyst set at 40 g. The test results are shown in Table 3 and FIG. 7.

Comparative Example 1

[Hydrothermal Synthesis of Raw Material Zeolite]

To a solution obtained by adding 0.05 kg of NaOH and 4.0 kg of water to 8 kg of a sodium silicate aqueous solution (manufactured by Fuji Kagaku Corp., SiO$_2$: 26% by mass, Na$_2$O: 7% by mass), a solution obtained by dissolving 0.61 kg of aluminum sulfate hexadecahydrate and 0.1 kg of 1,3-dimethyl urea in 15 kg of water was added under stirring, followed by adding 10 kg of 5% by mass of sulfuric acid, and thereby a homogeneous gel was obtained. The gel was charged in an autoclave having an inner volume of 50 L, a hydrothermal synthesis was conducted at 160° C. for 10 hours under stirring, followed by cooling a resulting slurry, and thereby a seed slurry was obtained.

To 12.6 kg of the resulting seed slurry, 5.3 kg of the sodium silicate aqueous solution used in the above, 30 g of NaOH and 2.67 kg of water were added. Further, a solution obtained by dissolving 0.41 kg of aluminum sulfate hexadecahydrate and 0.06 kg of 1,3-dimethyl urea in 10 kg of water was added under stirring, followed by adding 6.67 kg of 5% by mass of sulfuric acid, and thereby a homogeneous gel was obtained. The gel was charged in an autoclave having an inner volume of 50 L, and a hydrothermal synthesis was conducted at 150° C. for 30 hours under stirring to crystallize.

The resulting slurry was washed with water until pH of the filtrate became 9 or less while filtering by centrifugation, followed by drying at 120° C. for 20 hours, further followed by calcining in air at 550° C. for 3 hours, and thereby a powder of Na-type ZSM-5 zeolite was obtained. Furthermore, the dried material was used to prepare a 10% by mass slurry in a 1 N nitric acid aqueous solution and ion-exchanged at room temperature for 3 hours, followed by washing with water while filtering by centrifugation until pH became 4.5 or more, still further followed by drying at 120° C. for 20 hours, and thereby a powder of an H-type ZSM-5 zeolite was obtained.

Figure 8:
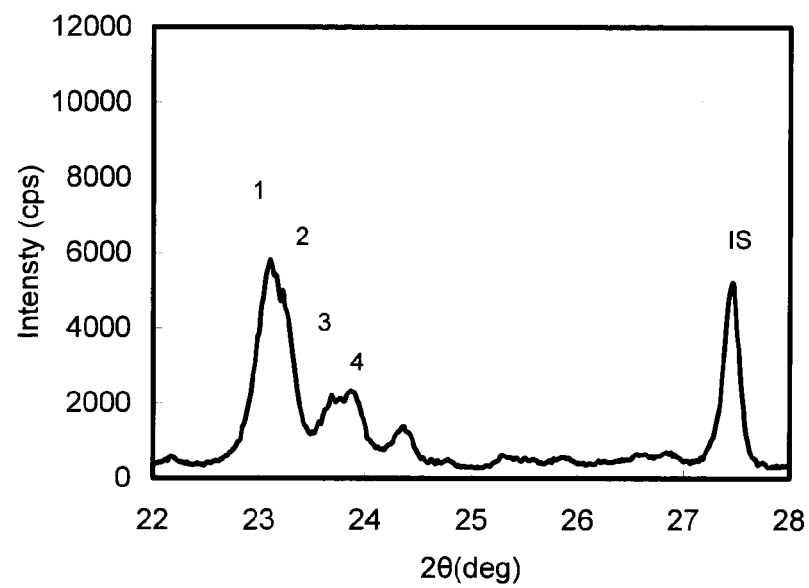
FIG. 8 shows a result of a crystallization index measurement (X-ray diffraction spectrum) of a zeolite used in Comparative Example 1.

To 5 g of the resulting H-type ZSM-5 zeolite, 1 g of rutile type titania was added, followed by kneading with an electrically-driven mortar for 30 min, and an X-ray diffraction spectrum of the resulting sample is shown in FIG. 8. From results of X-ray diffraction measurement, a crystallization index of the resulting H-type ZSM-5 zeolite was obtained and found to be 2.84. Furthermore, a silica/alumina molar ratio thereof was 33.

[Preparation of Zeolite-containing Catalyst]

The resulting H-type ZSM-5 zeolite was kneaded with silica sol, followed by extrusion molding. The content of the zeolite was 50% by mass. The resulting extrusion-molded catalyst was dried at 120° C. for 6 hours, followed by calcining at 700° C. for 2 hours, and thereby a columnar zeolite-containing molded catalyst having a diameter of 2 mm and a length of 3 to 5 mm was obtained. The resulting molded catalyst was ion-exchanged by stirring in a 0.5 N nitric acid aqueous solution, followed by washing with water, further followed by drying at 120° C. for 5 hours. A TPD acid amount of the resulting zeolite-containing molded catalyst was measured and found to be 105 μmol/g-zeolite.

[Production of Propylene]

In a stainless reaction tube having an inner diameter φ of 21.2 mm, 50 g of the resulting zeolite-containing molded catalyst was charged, and a water vapor treatment was conducted for 5 hours under the conditions of a temperature of 650° C., a steam flow rate of 107 g/hr, and a nitrogen flow rate of 200 NL/hr. A TPD acid amount of a water vapor-treated catalyst was measured and found to be 23 μmol/g-zeolite. In a stainless reaction tube having an inner diameter φ of 14.8 mm, 8 g of the water vapor-treated zeolite-containing molded catalyst was charged, and a reaction was conducted under the following conditions.

Raw material feeding rates: ethylene 4.64 NL/hr (flow rate based on standard conditions)
:hydrogen 4.58 NL/hr
:nitrogen 2.46 NL/hr
:water 2.78 g/hr
The reaction pressure: 0.14 MPa/G
Reaction temperature: 550° C.

Reaction results at 2 and 6 hours after the start of reaction were as shown below. In a catalyst that uses a zeolite having a small crystallization index like in the present Comparative Example, when a water vapor treatment at 650° C. and for 5 hours, which was conducted to compare the activity over time and degradation behavior with those of Examples 1 to 4, was conducted, remarkable activity degradation was recognized and the activity was low; accordingly, degradation behavior by repetition could not be evaluated.

| Reaction time (Hr) | 2.0 | 6.0 |
|---|---|---|
| Conversion rate of ethylene (% by mass) | 11.6 | 10.3 |

Figure 9:
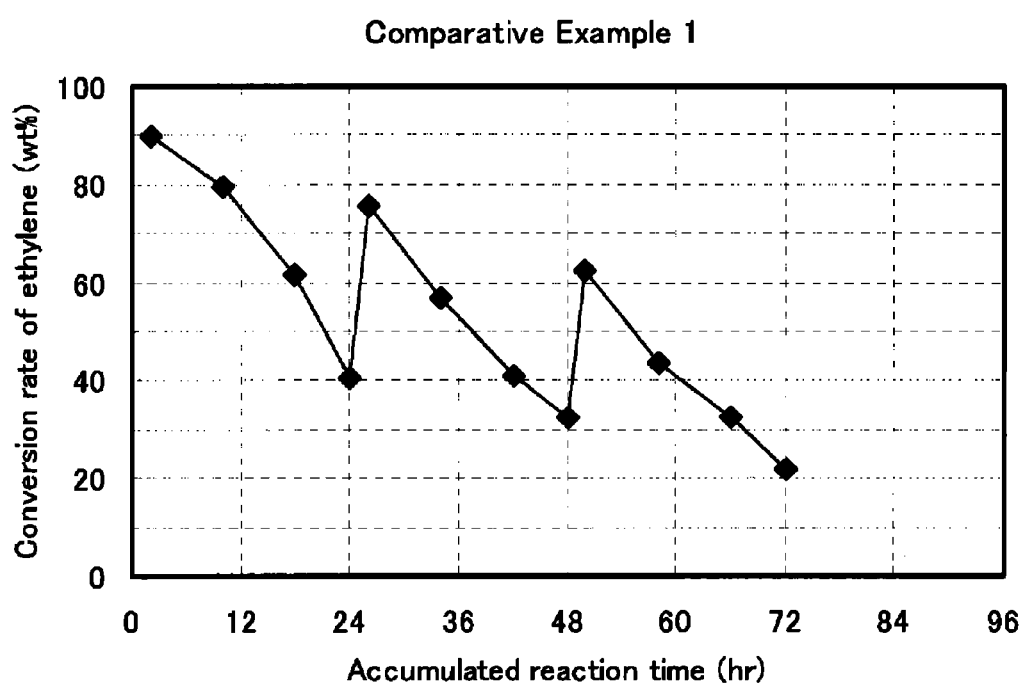
FIG. 9 shows a result of a reaction/regeneration repeating test in Comparative Example 1.

In the next place, in a stainless reaction tube having an inner diameter φ of 14.8 mm, 8 g of the zeolite-containing molded catalyst the same as the above (without steaming treatment) was charged, and a reaction was conducted under the same conditions. A reaction was continued for 24 hours. Thereafter, ethylene, feeding of hydrogen and water were stopped, and, while supplying nitrogen gas at 10 NL/hr, a temperature of a catalyst layer was set at 480° C. Thereafter, air was started supplying at 0.5 NL/hr and thereby coke deposited on the catalyst was combusted and removed (regeneration step). An oxygen concentration of an inlet gas at the start time was 1%. While monitoring CO and $CO_2$ concentrations in a gas at a reactor outlet by GC, with a total gas flow rate set constant, with flow rates of nitrogen and air varying, under the conditions shown below, catalyst regeneration (combustion and removal of deposited coke) was completed.
(1) Temperature: 480° C., oxygen concentration: 1%, 1 hour
(2) Temperature: 520° C., oxygen concentration: 1%, 3 hours
(3) Temperature: 550° C., oxygen concentration: 1%, 3 hours
(4) Temperature: 550° C., oxygen concentration: 5%, 1 hour
(5) Temperature: 580° C., oxygen concentration: 5%, 2 hours According to the method described above, with one cycle of a 24 hours reaction and a 10 hours regeneration, 3 cycles were repeated. The test results are shown in Table 4 and FIG. 9.

From the present Comparative Example, it is found that when a zeolite having a zeolite crystallization index of less than 3.3 is used, a catalyst is remarkably degraded and cannot be used repeatedly.

Example 6

[Hydrothermal Synthesis of Raw Material Zeolite]

In a solution obtained by dissolving 130 g of ethyl silicate in 278 g of ethanol, 291 g of a 10% by mass tetrapropyl ammonium hydroxide aqueous solution in which 1.5 g of aluminum sulfate hexadecahydrate was dissolved was added. The mixed solution was mixed and stirred for 10 min at 5000 rpm with a homogenizer and thereby a homogeneous transparent solution was obtained. Into a 1 L autoclave, 350 g of the solution was charged, and a hydrothermal synthesis was conducted at 125° C. for 110 hours under stirring at 500 rpm to crystallize.

The resulting slurry was washed with water while filtering until pH of the filtrate became 9 or less, followed by drying at 120° C. for 20 hours, further followed by calcining at 550° C. in air for 3 hours. Furthermore, the dried substance was used to prepare a 10% by mass slurry in a 1 N nitric acid aqueous solution and ion-exchanged at room temperature for 3 hours, followed by filtering and washing with water, further followed by drying at 120° C. for 10 hours, and thereby a powder of H-type ZSM-5 zeolite was obtained.

Figure 10:
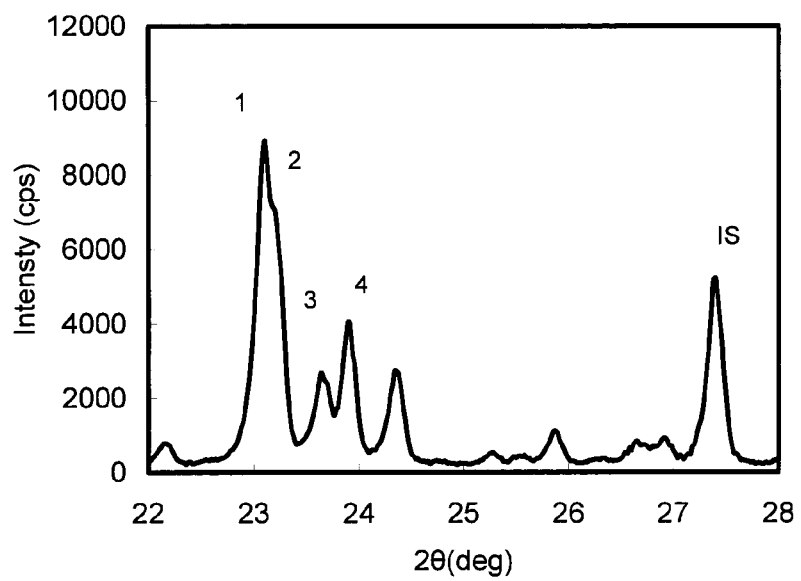
FIG. 10 shows a result of a crystallization index measurement (X-ray diffraction spectrum) of a zeolite used in Example 6.

To 5 g of the resulting H-type ZSM-5 zeolite, 1 g of rutile type titania was added, followed by kneading with an electrically-driven mortar for 30 min, and an X-ray diffraction spectrum of the resulting sample is shown in FIG. 10. From results of X-ray diffraction measurement, a crystallization index of the H-type ZSM-5 zeolite was obtained as 4.37. Furthermore, a silica/alumina molar ratio thereof was 290.

[Preparation of Zeolite-containing Catalyst]

The resulting H-type ZSM-5 zeolite was kneaded with silica sol, followed by extrusion molding. The content of zeolite was 50% by mass. The resulting extrusion-molded catalyst was dried at 120° C. for 6 hours, followed by calcining at 700° C. for 2 hours, and thereby a columnar zeolite-containing molded catalyst having a diameter of 2 mm and a length of 3 to 5 mm was obtained. The resulting zeolite-containing molded catalyst was ion-exchanged by stirring in a 0.5 N nitric acid aqueous solution, followed by washing with water, further followed by drying at 120° C. for 5 hours. A TPD acid amount of the resulting zeolite-containing molded catalyst was measured and found to be 77 μmol/g-zeolite.

[Production of Propylene]

In a stainless reaction tube having an inner diameter φ of 14.8 mm, 8 g of the resulting zeolite-containing molded catalyst was charged and a reaction was conducted under the following conditions.

Raw material feeding rates: ethylene 4.64 NL/hr (flow rate based on standard conditions)
:hydrogen 4.58 NL/hr
:nitrogen 2.46 NL/hr
:water 2.78 g/hr
Reaction pressure: 0.14 MPa/G
Reaction temperature: 550° C.

Figure 11:
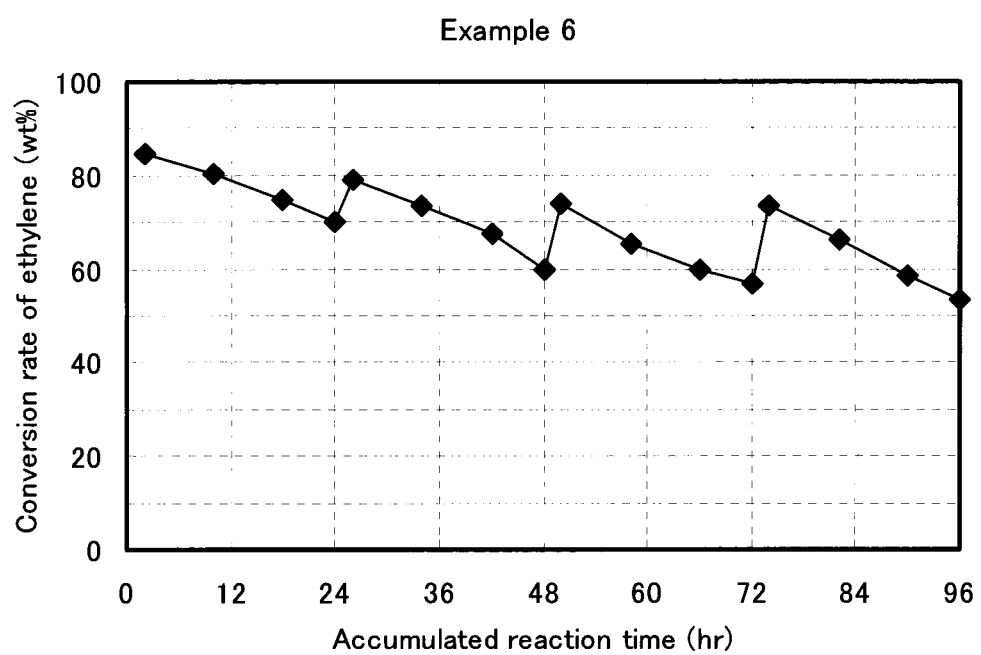
FIG. 11 shows a result of a reaction/regeneration repeating test in Example 6.

The reaction was continued for 24 hours. Thereafter, ethylene, hydrogen and water were stopped supplying, and, while supplying nitrogen gas at 10 NL/hr, a temperature of a catalyst layer was set at 480° C. Thereafter, air was started supplying at 0.5 NL/hr and thereby coke deposited on the catalyst was combusted and removed (regeneration step). An oxygen concentration of an inlet gas at the start time was 1%. While monitoring CO and $CO_2$ concentrations in a gas at a reactor outlet by GC, with a total gas flow rate set constant, with flow rates of nitrogen and air varying, under the conditions shown below, catalyst regeneration (combustion and removal of deposited coke) was completed.
(1) Temperature: 480° C., oxygen concentration: 1%, 1 hour
(2) Temperature: 520° C., oxygen concentration: 1%, 3 hours
(3) Temperature: 550° C., oxygen concentration: 1%, 3 hours
(4) Temperature: 550° C., oxygen concentration: 5%, 1 hour
(5) Temperature: 580° C., oxygen concentration: 5%, 2 hours According to the method described above, with one cycle of a 24 hours reaction and a 10 hours regeneration, three cycles were repeated. The test results are shown in Table 5 and FIG. 11.

Comparative Example 2

An $NH_4$-type MFI zeolite CBV2802 (trade name, manufactured by Zeolyst International Company, silica/alumina molar ratio: 280) was kneaded with silica sol, followed by extrusion molding. The content of zeolite was 50% by mass. The resulting extrusion-molded catalyst was dried at 120° C. for 6 hours and thereafter calcined at 700° C. for 2 hours and thereby a columnar zeolite-containing molded catalyst having a diameter of 2 mm and a length of 3 to 5 mm was obtained. The resulting molded catalyst was ion-exchanged by stirring in a 0.5 N nitric acid aqueous solution, followed by washing with water, further followed by drying at 120° C. for 5 hours. A TPD acid amount of the resulting zeolite-containing molded catalyst was measured and found to be 90 μmol/g-zeolite.

Figure 12:
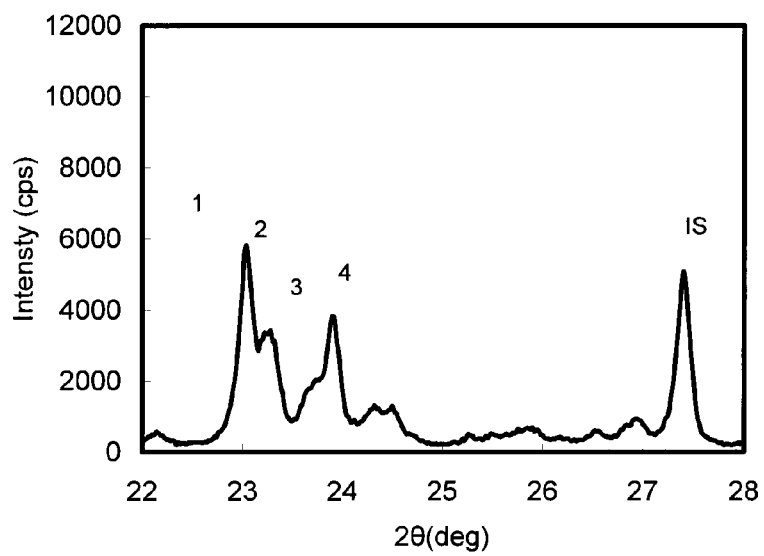
FIG. 12 shows a result of a crystallization index measurement (X-ray diffraction spectrum) of a zeolite used in Comparative Example 2.

A crystallization index of the zeolite was 2.90. An X-ray diffraction spectrum is shown in FIG. 12.

Figure 13:
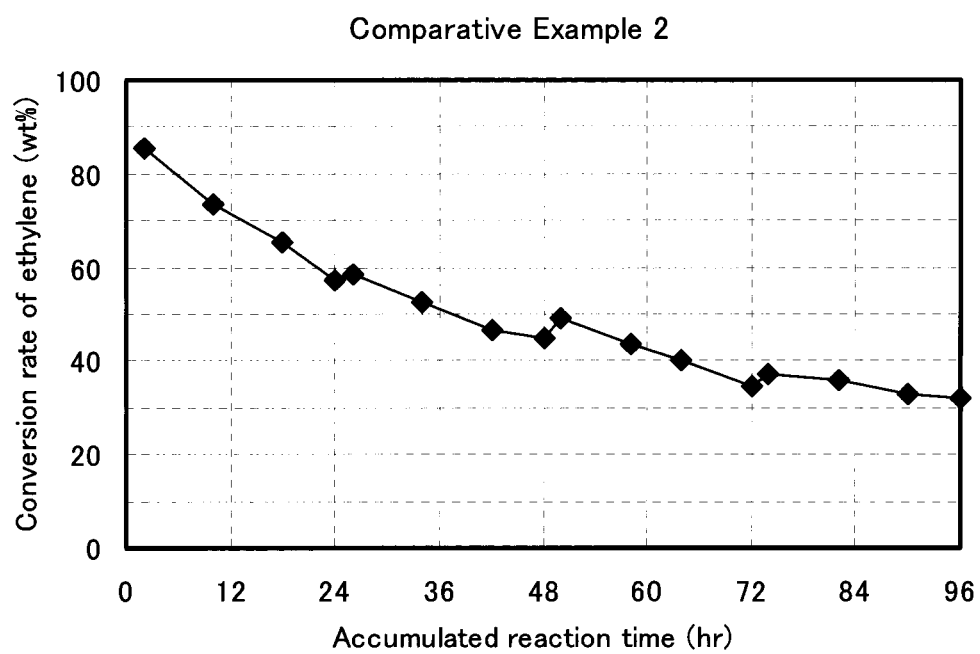
FIG. 13 shows a result of a reaction/regeneration repeating test in Comparative Example 2.

The reaction/regeneration repeating test was repeated four cycles in a manner similar to Example 1 except that the resulting zeolite-containing molded catalyst was used without water vapor treatment (steaming). The test results are shown in Table 6 and FIG. 13.

From the comparison between the present Comparative Example and Example 6, it is found that even a zeolite having a high silica/alumina ratio, when its crystallization index is less than 3.3, the catalyst is remarkably degraded and cannot be repeatedly used.

TABLE 1

| Cycle (times) | Reaction time (Hrs) | Conversion rate of ethylene (wt %) | Yield of propylene (wt %) |
|---|---|---|---|
| 1 | 2 | 69.5 | 26.8 |
|   | 10 | 67.8 | 26.4 |
|   | 18 | 62.9 | 26.0 |
|   | 24 | 59.6 | 25.2 |
| 2 | 2 | 66.3 | 25.9 |
|   | 10 | 62.2 | 25.2 |
|   | 18 | 58.0 | 24.6 |
|   | 24 | 56.4 | 23.4 |
| 3 | 2 | 67.5 | 25.8 |
|   | 10 | 64.4 | 26.2 |
|   | 18 | 61.0 | 25.5 |
|   | 24 | 56.4 | 24.4 |
| 4 | 2 | 68.3 | 26.5 |
|   | 10 | 62.9 | 25.6 |
|   | 18 | 61.4 | 25.6 |
|   | 24 | 57.3 | 24.5 |

TABLE 2

| Cycle (times) | Reaction temperature (°C.) | Reaction time (Hrs) | Conversion rate of ethylene (wt %) | Yield of propylene (wt %) |
|---|---|---|---|---|
| 1 | 520 | 2 | 67.3 | 26.0 |
|   |   | 10 | 64.3 | 25.4 |
|   |   | 18 | 62.3 | 24.2 |
|   |   | 24 | 60.1 | 23.9 |
| 2 | 580 | 2 | 66.6 | 27.7 |
|   |   | 10 | 63.3 | 27.0 |
|   |   | 18 | 57.7 | 25.9 |
|   |   | 24 | 53.2 | 24.6 |
| 3 | 520 | 2 | 66.6 | 25.8 |
|   |   | 10 | 63.9 | 24.3 |
|   |   | 18 | 62.0 | 23.8 |
|   |   | 24 | 60.6 | 23.4 |

TABLE 3

| Cycle (times) | Reaction time (Hrs) | Conversion rate of ethylene (wt %) | Yield of propylene (wt %) |
|---|---|---|---|
| 1 | 2 | 79.4 | 24.7 |
|   | 10 | 68.9 | 26.5 |
|   | 18 | 61.0 | 25.8 |
|   | 24 | 54.5 | 24.1 |
| 2 | 2 | 74.7 | 25.9 |
|   | 10 | 65.1 | 26.4 |
|   | 18 | 56.3 | 24.3 |
|   | 24 | 49.6 | 22.4 |
| 3 | 2 | 71.1 | 26.6 |
|   | 10 | 59.6 | 25.3 |
|   | 22 | 47.7 | 21.8 |
|   | 24 | 46.3 | 21.3 |
| 4 | 2 | 69.1 | 26.6 |
|   | 10 | 60.3 | 25.3 |
|   | 18 | 52.2 | 23.1 |
|   | 24 | 47.1 | 21.6 |

TABLE 4

| Cycle (times) | Reaction time (Hrs) | Conversion rate of ethylene (wt %) | Yield of propylene (wt %) |
|---|---|---|---|
| 1 | 2 | 89.9 | 9.7 |
|   | 10 | 79.5 | 20.6 |
|   | 18 | 61.6 | 24.0 |
|   | 24 | 40.8 | 15.4 |
| 2 | 2 | 75.7 | 24.2 |
|   | 10 | 56.9 | 21.7 |
|   | 18 | 41.2 | 16.1 |
|   | 24 | 32.6 | 13.0 |
| 3 | 2 | 62.2 | 24.6 |
|   | 10 | 43.7 | 18.3 |
|   | 18 | 32.5 | 13.3 |
|   | 24 | 22.0 | 9.0 |

TABLE 5

| Cycle (times) | Reaction time (Hrs) | Conversion rate of ethylene (wt %) | Yield of propylene (wt %) |
|---|---|---|---|
| 1 | 2 | 84.6 | 17.6 |
|   | 10 | 80.2 | 23.2 |
|   | 18 | 74.8 | 26.3 |
|   | 24 | 70.0 | 26.8 |
| 2 | 2 | 79.1 | 25.0 |
|   | 10 | 73.7 | 27.0 |
|   | 18 | 67.6 | 26.3 |
|   | 24 | 60.0 | 23.0 |
| 3 | 2 | 74.0 | 27.0 |
|   | 10 | 65.2 | 26.0 |
|   | 18 | 60.0 | 22.8 |
|   | 24 | 57.0 | 22.0 |
| 4 | 2 | 73.3 | 27.1 |
|   | 10 | 66.1 | 26.1 |
|   | 18 | 58.4 | 22.8 |
|   | 24 | 53.2 | 21.2 |

TABLE 6

| Cycle (times) | Reaction time (Hrs) | Conversion rate of ethylene (wt %) | Yield of propylene (wt %) |
|---|---|---|---|
| 1 | 2 | 85.6 | 20.3 |
|   | 10 | 73.5 | 24.0 |
|   | 18 | 65.4 | 24.2 |
|   | 24 | 57.3 | 23.2 |
| 2 | 2 | 58.6 | 23.4 |
|   | 10 | 52.5 | 21.2 |
|   | 18 | 46.6 | 19.4 |
|   | 24 | 44.9 | 18.8 |
| 3 | 2 | 49.0 | 20.9 |
|   | 10 | 43.7 | 18.4 |
|   | 18 | 40.1 | 16.8 |
|   | 24 | 34.8 | 14.5 |
| 4 | 2 | 37.1 | 15.9 |
|   | 10 | 35.7 | 15.6 |
|   | 18 | 33.1 | 14.0 |
|   | 24 | 32.0 | 13.6 |

The present application is based on Japanese Patent Application (Patent Application No. 2009-048369) filed at the Japanese Patent Office on Mar. 2, 2009, and the contents thereof are incorporated herein by reference.

Industrial Applicability

The method of the present invention for producing propylene permits producing propylene efficiently and stably over the long term from a hydrocarbon raw material containing ethylene in an amount exceeding 50% by mass while supplying water in an amount of 10% by mass or more based on a hydrocarbon raw material, and is also useful as an industrial production method from the viewpoint of the diversity of the raw materials for producing propylene.

The invention claimed is:

1. A method for producing propylene comprising:
    catalytically converting a hydrocarbon raw material containing ethylene in an amount exceeding 50% by mass with a zeolite-containing catalyst at a reaction temperature of 520° C. to 600° C. while supplying water,
    wherein a zeolite contained in the zeolite-containing catalyst satisfies (1) to (3) below;
    (1) the zeolite is an MFI zeolite,
    (2) a zeolite crystallization index obtained from an X-ray diffraction spectrum is 3.3 or more, and
    (3) a molar ratio of silica/alumina ($SiO_2/Al_2O_3$) is 20 to 300.

2. The method for producing propylene according to claim 1, wherein water is supplied in an amount of 10% by mass or more based on the hydrocarbon raw material.

3. The method for producing propylene according to claim 1 or 2, further comprising:
    heat-treating the zeolite-containing catalyst at a temperature equal to or more than 550° C.

4. The method for producing propylene according to claim 1 or 2, further comprising:
    heat-treating the zeolite-containing catalyst at a temperature equal to or more than 300° C. under the presence of water vapor.

5. The method for producing propylene according to claim 1 or 2, wherein the zeolite-containing catalyst contains at least one kind of metal element selected from the group consisting of elements belonging to group IB in the periodic table.

6. The method for producing propylene according to claim 1 or 2, further comprising:
    combusting coke adhered to the zeolite-containing catalyst.

* * * * *